United States Patent [19]

Su

[11] Patent Number: 5,874,789
[45] Date of Patent: Feb. 23, 1999

[54] CIRCUIT FOR INTEGRATING A LOCAL SWITCH AND A REMOTE-CONTROL SWITCH

[76] Inventor: Chih-Hai Su, No. 72-10, Chianan Li, Shanhua Chen, Tainan Hsien, Taiwan

[21] Appl. No.: 796,678

[22] Filed: Feb. 6, 1997

[30] Foreign Application Priority Data

Apr. 5, 1996 [JP] Japan ...................................... 8-083767

[51] Int. Cl.⁶ .................................................. H02J 13/00
[52] U.S. Cl. ............................ 307/141; 307/140; 307/86; 340/825.72; 361/160
[58] Field of Search ...................................... 307/141, 115, 307/140, 29, 114, 86; 340/825.69, 825.72; 361/160

[56] References Cited

U.S. PATENT DOCUMENTS 3,794,888  2/1974  Hisano ...................................... 307/114
3,869,651  3/1975  Long et al. ............................... 361/210
4,367,510  1/1983  Watanabe ................................. 361/160
5,309,310  5/1994  Baer et al. ................................ 361/42
5,381,049  1/1995  Onuma ..................................... 307/86

Primary Examiner—Albert W. Paladini

[57] ABSTRACT

The present invention relates to a circuit for integrating a local switch and a remote-control switch, primarily comprising a remote-control circuit, a first trigger circuit, a second trigger circuit, an integrating unit and a power circuit, in which the integrating unit further comprises two timer circuits, a local switch detecting circuit, a switching circuit and a power supplement circuit. When the circuit described above is in an initial state, in the event of the local switch does not operate within a certain time period, the control priority belongs to the remote-control circuit. When a user controls a load by remote control, the remote-control circuit will send a signal to reset the local switch detecting circuit and to make the output signal of the remote-control circuit be the control source of the switching circuit directly.

13 Claims, 5 Drawing Sheets

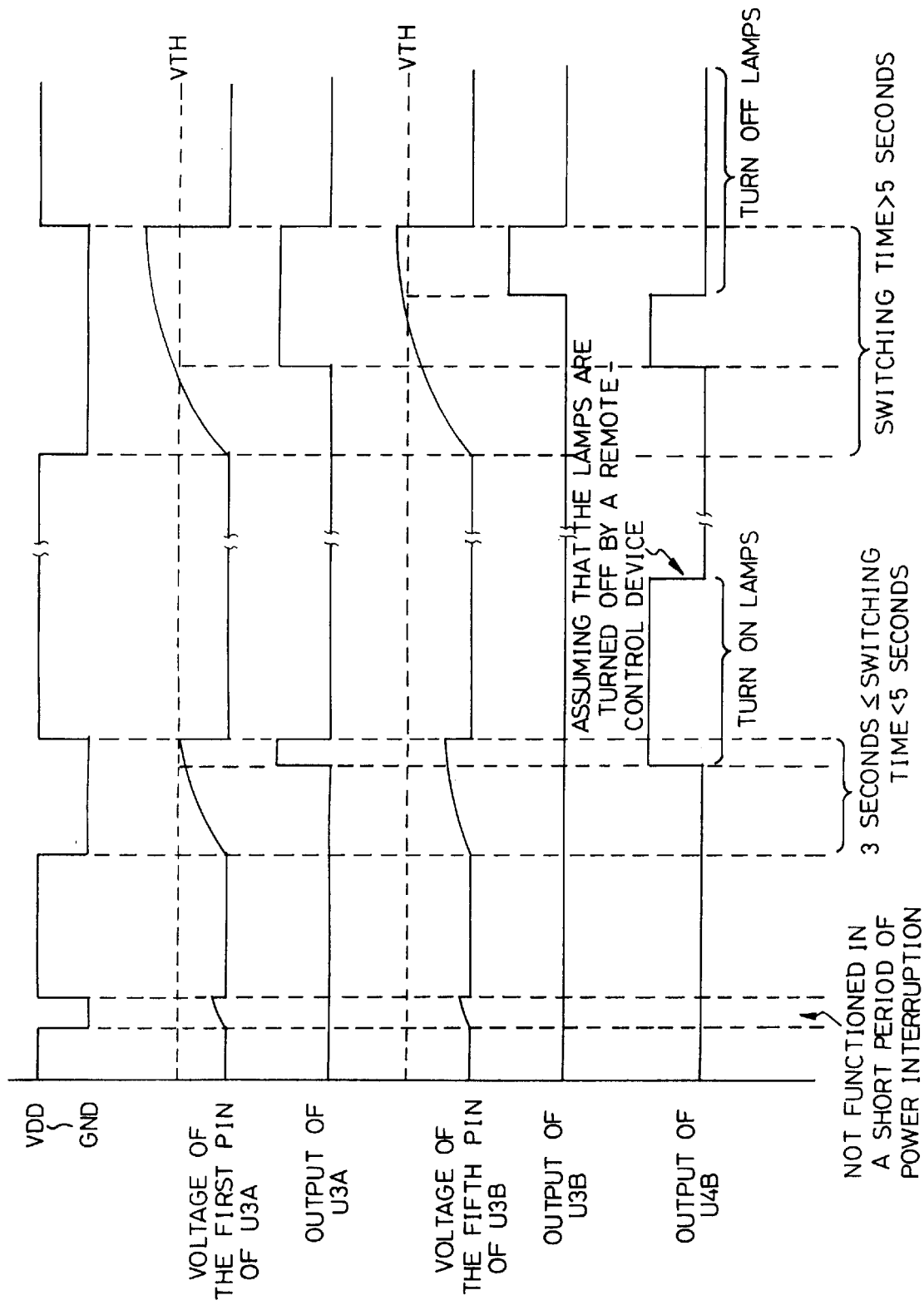

5,874,789

CIRCUIT FOR INTEGRATING A LOCAL SWITCH AND A REMOTE-CONTROL SWITCH

BACKGROUND OF THE INVENTION

The present invention relates to a circuit for integrating a local switch and a remote-control switch and, more particularly, to a circuit design being capable of integrating and selectively recognizing a control priority between a local switch and a remote-control switch.

The remote-control technology is generally used as well as a convenient way of controlling electronic appliances. Presently, such a technology has been extensively applied to general household appliances, such as a television, a high fidelity stereo, a video recorder and the like.

But there is no hiding the fact that, even though the remote-control technology is convenient to everybody, in fact, there are still many household appliances that do not yet have a remote-control function provided, for example, a set of lamps, a ceiling fan, etc., and they are still controlled by the local switches set on the wall. Since they can not be controlled in the same way as utilized by the household facilities with a remote-control function, that is, by remote controlling rather than a local switch, there still exist some inconveniences.

To remedy this shortcoming, an attachment type of remote-control device has appeared on the market for providing the remote-control function to equipment originally without the remote-control ability provided. However, an original local switch can not be utilized once a remote-control device has been installed on such equipment and inconveniences in this type of control still remain. Both of the local switch function and the remote-control function that are achieved by these types of equipment at the same time can be achieved through remodeling them. The remodeling technology is rather complicated and electricians are often expensive. Additionally, how to make the control signals of the local switch and the remote-control switch compatible and how to avoid a situation of mutual conflicts are also problems in the aspect of the remote-control technical application to be resolved.

SUMMARY OF THE INVENTION

Consequently, the primary objective of the present invention is to provide a circuit for integrating a local switch and a remote-control switch. By designing such a circuit, users can control a load through a local switch or a remote-control switch respectively and can effectively solve a problem created by signal integration.

Another objective of the present invention is to provide a circuit design for integrating the control signals of a local switch and a remote-control switch, mainly comprising a remote-control circuit, a first trigger circuit, a second trigger circuit, an integrating unit and a power circuit, in which the integrating unit further comprises a first timer circuit, a second timer circuit, a local switch detecting circuit, a switching circuit and a power supplement circuit. When starting, the circuit described above makes the remote-control circuit have the control priority if the local switch does not operate during a certain time period. When users control a load by a way of remote controlling, the remote-control circuit will send a signal indicating to reset the local switch detecting circuit and the output signal of the remote-control circuit will be directly made to be the control source of the switching circuit.

A further objective is to provide a circuit for integrating a local switch and a remote-control switch to prevent the misoperation, primarily two timer circuits are set in the integrating unit to eliminate a phenomenon of misoperation caused by a momentary power interruption.

BRIEF DESCRIPTION OF THE DRAWINGS

The above objectives, other features and advantages of the present invention will become more apparent by describing in detail a preferred embodiment thereof with reference to the attached drawings, in which:

FIG. 4 is a timing diagram of the integrating unit of the present invention.

DETAILED DESCRIPTION OF THE PREFERRED EMBODIMENT

Figure 1:
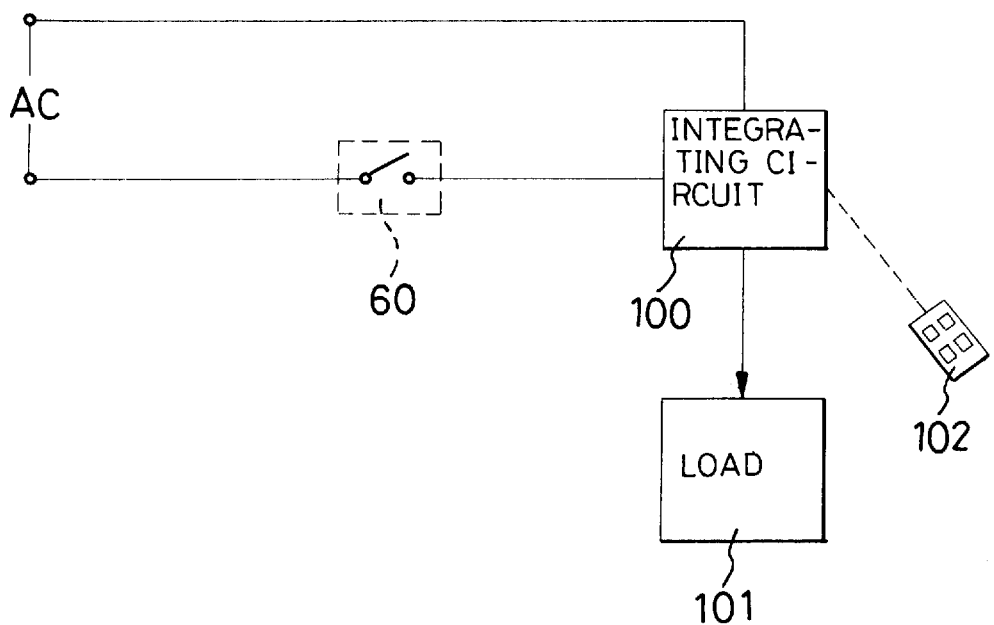
FIG. 1 is a schematic illustration of a system in accordance with the present invention.

First, as shown in FIG. 1, there is provided a system schematic illustration of the present invention, primarily a local switch 60 is in a series connection between a circuit 100 for integrating the local switch 60 and a remote-control switch 102 (hereinafter referred to as an integrating circuit) and an alternating current (hereinafter abbreviated as AC) power source. The local switch 60 is one kind of switch generally set on the wall and the output terminal of the integrating circuit 100 is connected to a load 101. The integrating circuit 100 itself has a remote-control circuit which can receive a remote control signal from a remote-control device 102 to manage the control of the load 101. In other words, the integrating circuit 100 is used to integrate the control signals between an internal remote-control switch and a local switch 60 for providing a consumer with the control of the load 101 by utilizing either the local switch 60 or the remote control.

Figure 2A:
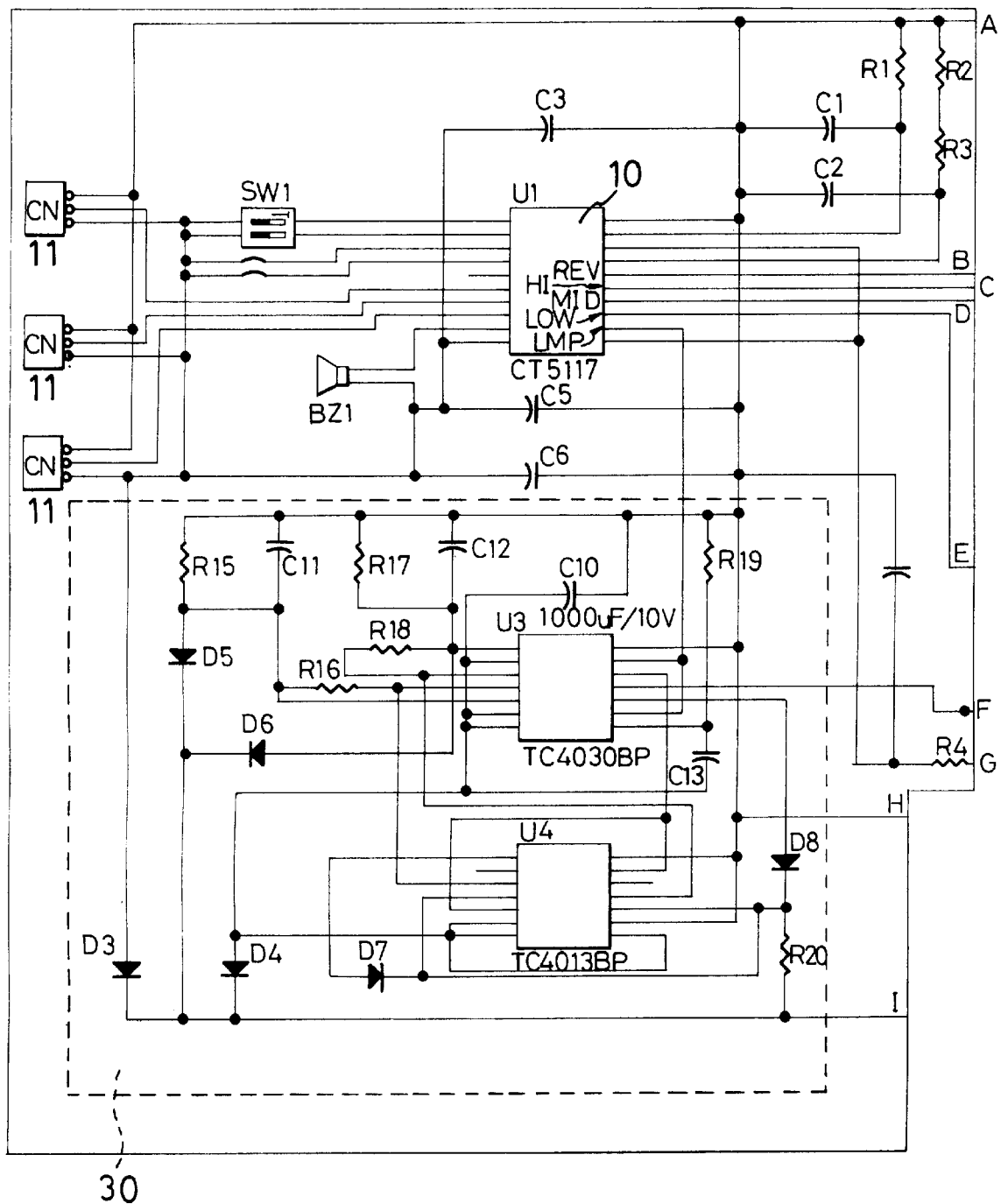
FIGS. 2A and 2B combine a detailed circuit diagram of the present invention.
Figure 2B:
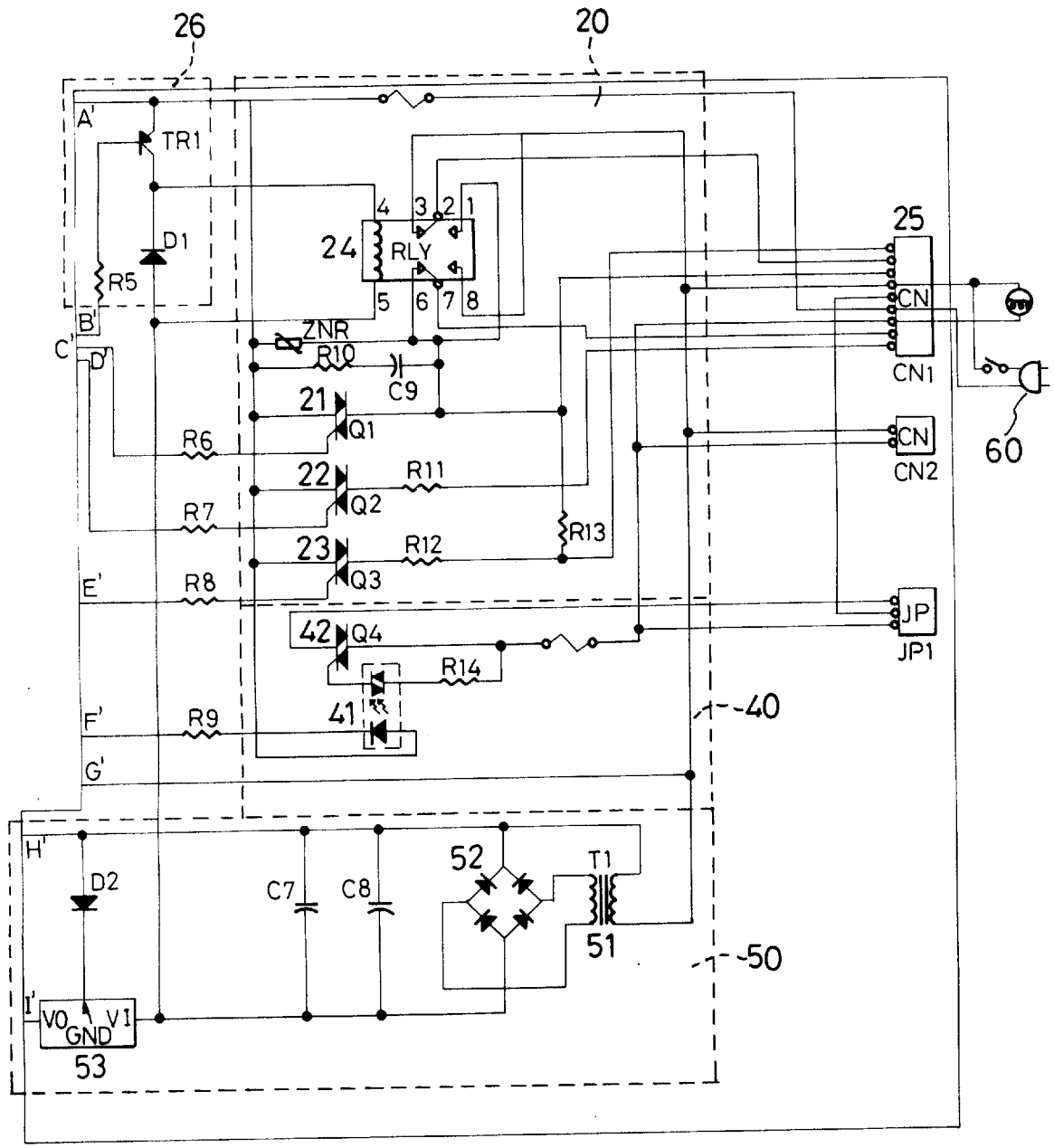

Referring to FIGS. 2A and 2B, a detailed circuit diagram of the integrating circuit 100 described above is shown, mainly comprising a remote-control circuit 10, a first trigger circuit 20, a second trigger circuit 40, an integrating unit 30 and a power circuit 50. For conveniently explaining the operating principle of the present invention, the control operation of the lamps and a ceiling fan having been practically applied whereby the operating principle will be illustrated here. As shown in FIG. 2B, the first and second trigger circuits, 20 and 40, described above will be used to separately control a motor of the ceiling fan and the lamps in which the first trigger circuit 20 is composed of three sets of thyristers 21–23 and a relay 24. These thyristers, 21–23, are connected to the motor of the ceiling fan by connecting anodes of the thyristers 21–23 to corresponding pins of a connector 25 respectively, and further, a gate of each one of the thyristers 21–23 is connected to the remote-control circuit 10. The rotating speed of the ceiling fan is set by separately controlling whether each one of the thyristers 21–23 is turned on or not.

The second trigger circuit 40 included of a photoelectric coupler 41 and a thyrister 42, in which an anode of the thyrister 42 is connected to the lamps through the connector 25, a gate of the thyrister 42 is connected to a detector of the photoelectric coupler 41 and a light source thereof is connected to the integrating unit 30.

The relay 24, as shown in FIG. 2B, is controlled by a transistor switching circuit 26 being connected to the remote-control circuit 10 and the rotating direction of the ceiling fan is controlled by controlling the triggered status thereof.

The remote-control circuit 10, as shown in FIG. 2A, includes an integrated circuit (hereinafter abbreviated as IC) numbered CT5117 and has functions of decoding and microprocessing for receiving the remote-control signals transmitted from the remote-control device 102 to trigger the other circuits through the corresponding output terminals. A trigger pin REV is connected to the first trigger circuit 20 to control the rotating direction of the ceiling fan by connecting to an input terminal, that is, a base of a transistor TR1, of the transistor switching circuit 26. Three output pins HI, MID and LO are respectively connected to gates of the three thyristors, 21–23, to set the rotating speed of the ceiling fan by selectively triggering one of the three thyristors, 21-23. An output signal pin LMP is connected to the integrating unit 30 and the operation status of the remote-control circuit 10 is output to the integrating unit 30 by the output signal pin LMP. Additionally, a plurality of connectors 11 connected to input pins of the remote-control circuit 10 are connected to a receiver. In a preferred embodiment of the present invention, this receiver is an infrared receiver.

Figure 3:
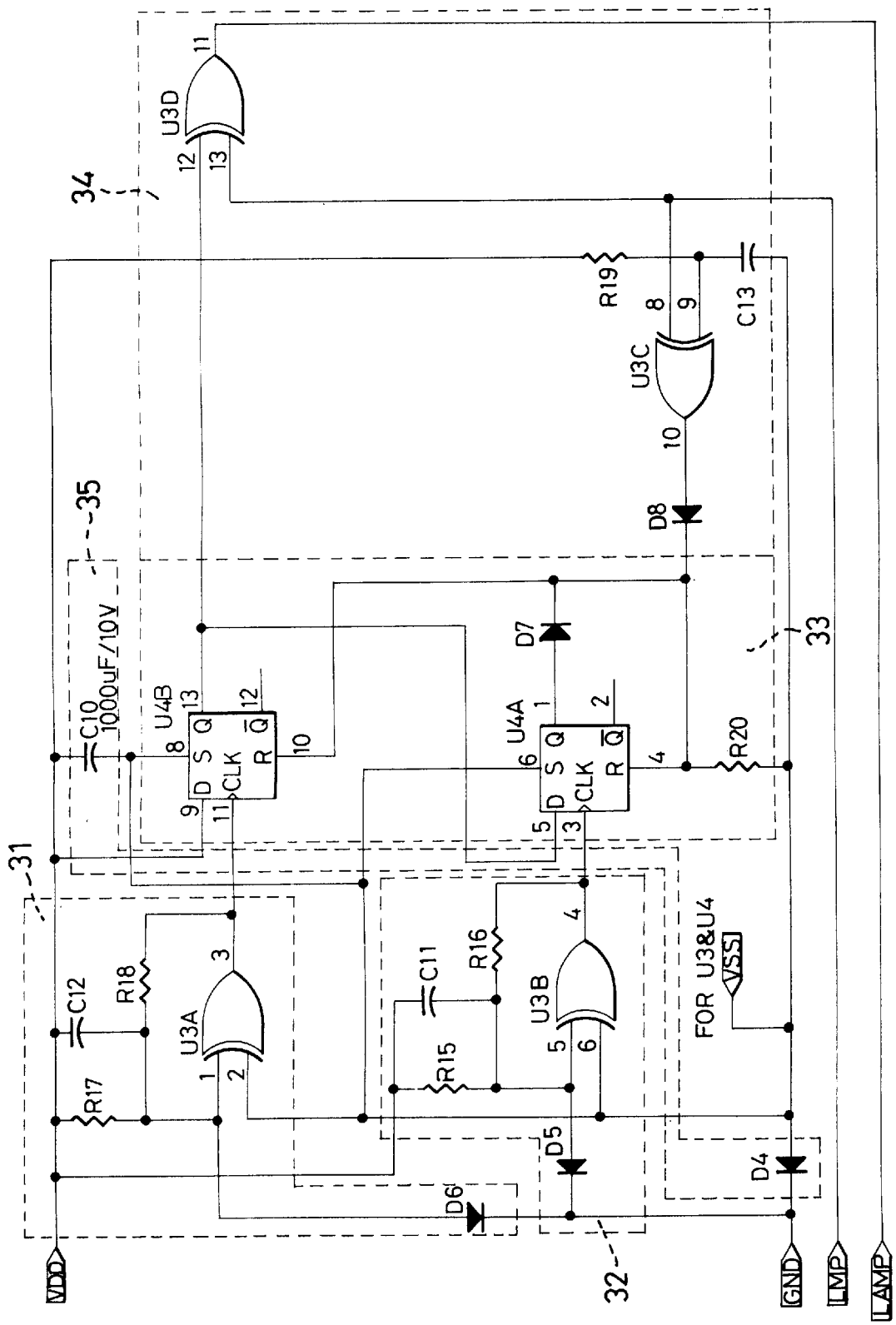
FIG. 3 is a further detailed circuit diagram of the integrating unit of the present invention.

The integrating unit 30, as shown in FIG. 2A, includes a flip-flop IC numbered TC4013BP and an Exclusive OR (abbreviated as XOR hereinafter) IC numbered TC4030BP, and in FIG. 3 shows a more detailed circuit diagram of the flip-flop IC and the XOR IC, including two timer circuits, a first timer circuit 31 and a second timer circuit 32, a local switch detecting circuit 33, a switching circuit 34 and a power supplement circuit 35. Each of the two timer circuits, 31 and 32, is a modified Schmidt circuit including an XOR gate, two resistors, a capacitor and a diode, and primarily eliminates a phenomenon of misoperation caused by a momentary power interruption. The first timer circuit 31 is a 3-second timer comprising a first XOR gate U3A, two resistors, R17 and R18, a capacitor C12 and a diode D6, and the second timer circuit 32 is a 5-second timer comprising a second XOR gate U3B, two resistors, R15 and R16, a capacitor C11 and a diode D5. The local switch detecting circuit 33 includes two flip-flops, a first flip-flop U4A and a second flip-flop U4B, a resistor R20 and a diode D7. Input clock terminals CLK of the first flip-flop U4A and the second flip-flop U4B are triggered by the output signals of the second XOR gate U3B and the first XOR gate U3A respectively. An output terminal of the first flip-flop U4A is connected to a reset input terminal through the diode 7 and an output terminal of the second flip-flop U4B is connected to a D input terminal of the first flip-flop U4A. The switching circuit 34 includes a reset circuit and a fourth XOR gate U3D, in which the reset circuit further includes a third XOR gate U3C, a resistor R19, a capacitor C13 and a diode D8 for generating a reset signal to make the outputs Q of the two flip-flops, U4A and U4B, to be both "0" when AC power source is turned on the first time, and the fourth XOR gate U3D is used for integrating an output signal from the second flip-flop U4B and a signal from the signal pin LMP of the remote-control circuit 10. Normally, the status of the signal pin LMP described above is "1", and the output terminal of the second flip-flop U4B is connected to one input terminal of the fourth XOR gate U3D while the other one input terminal thereof is connected to the signal pin LMP of the remote-control circuit 10 and the on/off status of the lamps is controlled by the output signal of the fourth XOR gate U3D. The power supplement circuit 35 includes a diode D4 and a capacitor C10, in which C10 is a capacitor with a very large capacity, 1000 $\mu$F/10V in the preferred embodiment, for supplying the power source to U3A, U3B, U4A and U4B during a momentary power interruption period.

The power circuit 50, as shown in FIG. 2B, includes a transformer 51, a bridge rectifier 52 and a regulated IC 53, and primarily provides the operation power source, such as $V_{DD}$, that the circuits described above require. The output terminal of the power circuit 50 is connected to the remote-control circuit 10 through a small capacity capacitor C6 as a power filtering circuit of the remote-control circuit 10.

The detailed circuit configuration of the present invention can be seen from the above description in conjunction with FIGS. 2A, 2B and FIG. 3. As to the way of operation, a preferred embodiment of the present invention having functions of turning on/off the lamps and controlling the ceiling fan incorporated with a timing diagram shown in FIG. 4 will be described below.

The lamps and the ceiling fan can be controlled by the local switch 60 and the remote-control circuit 10 by remote control respectively after the connector 25 has been connected to the lamps and an AC power source. In the circuit design described above, the remote-control circuit 10 is set to take priority of control first in the initial state of the circuit and the principle thereof is referred to FIG. 3. The outputs of the first and second XOR gates, both U3A and U3B, are "0" since the discharging effects of resistors R17, R18 and capacitor C12 as well as resistors R15, R16 and capacitor C11 do not reach a threshold voltage $V_{TH}$ level during a short period of power interruption. When the local switch 60 is turned off within 3 to 5 seconds, the output of the first XOR gate U3A becomes "1" due to the discharging results of the resistor R17 and the capacitor C12. The output Q of the second flip-flop U4B is triggered by the output signal of the first XOR gate U3A to change to "1" and the lamps are turned on after the output Q of the second flip-flop U4B is inverted by the fourth XOR gate U3D. If the switching time is equal to or greater than 5 seconds, the output Q of the second flip-flop U4B will first become "1" because the resistor R17 and the capacitor C12 are discharged first to reach the threshold voltage $V_{TH}$ level. In the meantime, the lamps are turned off since the local switch 60 is still in the turned off state. The output Q of the first flip-flop U4A is "0" when the resistor R15 and the capacitor C11 are discharged to reach the threshold voltage $V_{TH}$ level and then the output Q of the second flip-flop U4B becomes "0" once again immediately after the outputs of the first flip-flop U4A and the second flip-flop U4B are reset to "0". At the same time, the local switch 60 is turned on again while the lamps are still turned off.

Although the invention has been explained in relation to its preferred embodiment, it is to be understood that many other possible modifications and variations can be made without departing from the spirit and scope of the invention as hereinafter claimed.

I claim:

1. A circuit to integrate a local switch and a remote-control switch, comprising:
   a remote-control circuit having a signal terminal and a plurality of output terminals;
   a trigger circuit connected to a load, comprising a relay and a plurality of thyristors; and
   an integrating unit,
   wherein
      said integrating unit is connected to an external power source through said local switch,
      said remote-control circuit receives a remote-control signal transmitted from said remote-control switch to control said remote-control circuit, said plurality of output terminals of said remote-control circuit are connected to said trigger circuit to control said trigger circuit based upon said remote-control signal, and said signal terminal of said remote-control circuit is connected to said integrating unit, and the load is controlled under one of said local switch and said remote-control circuit based on said signal terminal of said remote-control circuit and in accordance with said remote-control signal.

2. The circuit as claimed in claim 1, wherein said remote-control circuit comprises an integrated circuit to decode and to microprocess the remote-control signal transmitted from said remote-control switch.

3. A circuit to integrate a local switch and a remote-control switch, comprising:

a remote-control circuit having a signal terminal and a plurality of output terminals;

a trigger circuit connected to a load; and an integrating unit comprising a first timer circuit, a second timer circuit, a local switch detecting circuit, a switching circuit and a power supplement circuit, wherein each of said first and second timer circuits comprises an Exclusive OR gate, two resistors, a capacitor and a diode to eliminate misoperation caused by a momentary power interruption, said local switch detecting circuit comprises a first flip-flop, a second flip-flop, a resistor and a diode, and input clock terminals of said first flip-flop and said second flip-flop are triggered by corresponding output signals from the Exclusive OR gate of said second timer circuit and the Exclusive OR gate of said first timer circuit, respectively, said switching circuit comprises a reset circuit and an Exclusive OR gate, and said Exclusive OR gate of said switching circuit integrates an output signal from said second flip-flop in said local switch detecting circuit and a signal from said signal terminal of said remote-control circuit to control an on and off status of the load, said power supplement circuit comprises a diode and a capacitor, said integrating unit of said circuit to integrate said local switch and said remote-control switch is connected to an external power source through said local switch, said remote-control circuit receives a remote-control signal transmitted from said remote-control switch to control said remote-control circuit, said plurality of output terminals of said remote-control circuit are connected to said trigger circuit to control said trigger circuit based upon said remote-control signal, and said signal terminal of said remote-control circuit is connected to said integrating unit, and the load is controlled under one of said local switch and said remote-control circuit based on said signal terminal of said remote-control circuit and in accordance with said remote-control signal.

4. The circuit as claimed in claim 3, wherein said first timer circuit is a 3-second timer and said second timer circuit is a 5-second timer.

5. The circuit as claimed in claim 3, wherein said reset circuit in said switching circuit comprises an Exclusive OR gate, a resistor, a capacitor and a diode to generate a reset signal to set outputs of said first and second flip-flops in said local switch detecting circuit to "0".

6. The circuit as claimed in claim 3, wherein said remote-control circuit comprises an integrated circuit to decode and to microprocess the remote-control signal transmitted from said remote-control switch.

7. The circuit as claimed in claim 3, wherein said capacitor in said power supplement circuit provides a power source to said first and second flip-flops in said local switch detecting circuit and to said Exclusive OR gates of said first and second timer circuits during a momentary power interruption period.

8. The circuit as claimed in claim 7, wherein said capacitor has a capacitance value greater than 1000 $\mu$F/10V.

9. The circuit as claimed in claim 7, wherein said capacitor has a capacitance value between 1000 $\mu$F/10V and 10000 $\mu$F/10V.

10. A circuit to integrate a local switch and a remote-control switch, comprising:

a remote-control circuit having a signal terminal and a plurality of output terminals;

a trigger circuit connected to a load, comprising a photoelectric coupler and a thyrister; and an integrating unit, wherein said integrating unit is connected to an external power source through said local switch, said remote-control circuit receives a remote-control signal transmitted from said remote-control switch to control said remote-control circuit, said plurality of output terminals of said remote-control circuit are connected to said trigger circuit to control said trigger circuit based upon said remote-control signal, and said signal terminal of said remote-control circuit is connected to said integrating unit, and the load is controlled under one of said local switch and said remote-control circuit based on said signal terminal of said remote-control circuit and in accordance with said remote-control signal.

11. The circuit as claimed in claim 10, wherein said remote-control circuit comprises an integrated circuit to decode and to microprocess the remote-control signal transmitted from said remote-control switch.

12. A circuit to integrate a local switch and a remote-control switch, comprising:

a remote-control circuit having a signal terminal and a plurality of output terminals;

a trigger circuit connected to a load;

an integrating unit; and a power circuit to provide an internal power source required by said remote-control circuit, said trigger circuit and said integrating unit, said power circuit including a transformer, a bridge rectifier and a regulated integrated circuit, wherein said integrating unit is connected to an external power source through said local switch, said remote-control circuit receives a remote-control signal transmitted from said remote-control switch to control said remote-control circuit, said plurality of output terminals of said remote-control circuit are connected to said trigger circuit to control said trigger circuit based upon said remote-control signal, and said signal terminal of said remote-control circuit is connected to said integrating unit, and the load is controlled under one of said local switch and said remote-control circuit based on said signal terminal of said remote-control circuit and in accordance with said remote-control signal.

13. The circuit as claimed in claim 12, wherein said remote-control circuit comprises an integrated circuit to decode and to microprocess the remote-control signal transmitted from said remote-control switch.

* * * * *